US008500708B2

(12) United States Patent
Glenn

(10) Patent No.: US 8,500,708 B2
(45) Date of Patent: Aug. 6, 2013

(54) COMPACT PORTABLE URINAL APPARATUS, KIT CONTAINING THE SAME AND METHODS OF USING THE SAME

(76) Inventor: Lawrence Glenn, Harvey, IL (US)

( * ) Notice: Subject to any disclaimer, the term of this patent is extended or adjusted under 35 U.S.C. 154(b) by 528 days.

(21) Appl. No.: 12/779,149

(22) Filed: May 13, 2010

(65) Prior Publication Data

US 2011/0060297 A1 Mar. 10, 2011

Related U.S. Application Data

(60) Provisional application No. 61/276,122, filed on Sep. 8, 2009.

(51) Int. Cl.
*A61F 5/453* (2006.01)
*A61G 9/00* (2006.01)
*A47K 11/12* (2006.01)

(52) U.S. Cl.
USPC .............. 604/349; 604/350; 4/144.1; 4/144.2

(58) Field of Classification Search
USPC ................................ 4/144.1–144.4; 604/317
See application file for complete search history.

(56) References Cited

U.S. PATENT DOCUMENTS 1,386,696 A * 8/1921 Fishback ........................ 4/144.1
2,593,051 A 4/1952 Pearcy
3,306,515 A 2/1967 Beaumont
3,403,410 A 10/1968 Benzel et al.
3,403,715 A 10/1968 Trudel
3,535,714 A 10/1970 Bjork
3,597,770 A 8/1971 Jacuzzi
3,633,581 A 1/1972 Welch
3,797,734 A 3/1974 Fleury et al.
4,309,779 A * 1/1982 Knight ........................... 4/144.3
5,056,932 A 10/1991 Young
5,065,459 A 11/1991 Tjahaja
5,067,821 A 11/1991 Young
5,116,139 A 5/1992 Young et al.
5,354,132 A 10/1994 Young et al.
5,356,398 A 10/1994 Willis
5,745,926 A 5/1998 Cailleteau
6,132,407 A * 10/2000 Genese et al. ................ 604/327
6,163,892 A * 12/2000 Abbato .......................... 4/144.1
6,199,220 B1 3/2001 Smith
6,324,704 B1 12/2001 Imo
6,345,911 B1 2/2002 Young et al.
6,968,577 B1 * 11/2005 Taft, Jr. .......................... 4/144.1
7,513,894 B2 * 4/2009 Howlett ........................ 604/355
7,530,121 B2 5/2009 Snider
2006/0036224 A1 * 2/2006 Suh et al. ...................... 604/367

* cited by examiner

*Primary Examiner* — Susan Su
(74) *Attorney, Agent, or Firm* — Scherrer Patent & Trademark Law, P.C.; Stephen T. Scherrer

(57) ABSTRACT

A compact portable container apparatus holds urine or other fluids safely and hygienically. Specifically, a container is provided that traps urine or other fluids when deposited therein. The container has one or more seals that allows the container to be sealed after use so that leakage of the container after use is minimized or eliminated. Moreover, the container has a generally horizontally disposed downwardly sloping passageway for the passage of urine or other fluids and an angled or arcuately-shaped wall for directing a flow or spray of urine or other fluids into a reservoir for holding the same. Moreover, the container has a window for viewing the contents of the container to determine the quantity of fluids contained therein. Alternatively, the container includes an absorbent material for absorbing the urine or other fluids. The container may be made from a soft, resilient thermoplastic material. A kit is provided including the container and other articles, such as wet napkins, cleaning wipes, sickness bags and/or other like articles. Methods of using the same are further provided.

12 Claims, 5 Drawing Sheets

COMPACT PORTABLE URINAL APPARATUS, KIT CONTAINING THE SAME AND METHODS OF USING THE SAME

The present invention claims priority to U.S. Provisional Patent Application No. 61/276,122, filed on Sep. 8, 2009, which is incorporated herein in its entirety.

TECHNICAL FIELD

The present invention relates to a compact portable urinal apparatus for holding urine or other fluids safely and hygienically. Specifically, the present invention provides a container that traps urine or other fluids when deposited therein. The container has one or more seals that allow the container to be sealed after use so that leakage of the container after use is minimized or eliminated. Moreover, the container has a generally horizontal downwardly sloping passageway for the passage of urine or other fluids and an angled or arcuately-shaped backwall for directing a flow or spray of urine or other fluids downward into a reservoir or holding area for holding the same. Moreover, the present invention provides a container having a window for viewing the contents of the container to determine how full the container may be. The container may include an absorbent material for absorbing the urine or other fluids. The container may be made from a soft, resilient material, such as a flexible thermoplastic material. The present invention further relates to a kit having the container and other components, such as wet napkins, cleaning wipes, sickness bags and/or other like components. In addition, the present invention relates to methods of using the same.

BACKGROUND

It is, of course, generally known for a person to require a receptacle for depositing urine or other fluids thereinto, especially when the person has an urge to urinate. It is generally difficult to hold urine for extended periods of time and a person may find that urination is necessary even when a bathroom is not present. For example, modern people take many extended trips or travel routinely, either by car, plane or train. In many cases, a person may need to excrete when it is not convenient and a bathroom is not available.

Moreover, even if a bathroom is generally available, many individuals have mobility issues that make it difficult for the individual to relieve himself. For example, a person who is sick, or paralyzed, or otherwise confined to a bed or other location may not be able to travel to a bathroom, when necessary.

Solutions to this problem include absorbent undergarments, such as diapers and the like so that an individual may urinate into the absorbent undergarment. However, use of absorbent undergarments does nothing to remove the urine or other bodily fluids from the person until the undergarment is removed. Wearing an undergarment that is full of urine and/or other bodily fluids is uncomfortable, may give rise to the formation of odors, is very unsanitary and is not unhygienic.

It is further generally known to provide a portable container that an individual may urinate into. However, the containers typically are used by positioning the container vertically with a user urinating straight down thereinto to catch the urine and minimize spillage of the same. Moreover, typical portable urinals do not properly seal the containers to minimize or eliminate spillage of urine and/or other bodily fluids therefrom.

In addition, known portable containers for holding urine or other fluids may typically be made from hard plastic or metal material making it difficult to store and further being uncomfortable for an individual to use. Moreover, it is oftentimes difficult to determine how full a known portable container may be, and whether the container may be utilized one or more times based on the contents thereof.

A need, therefore, exists for an apparatus for holding urine and/or other bodily fluids that may be utilized generally horizontally, such that the container can be utilized to catch and hold urine, especially from a user in a sitting position.

In addition, a need exists for an apparatus for holding urine or other fluids that catches and holds a spray of urine or other fluids and directs the spray of urine or other fluids into a holding area or reservoir.

Moreover, a need exists for an apparatus for holding urine or other fluids that provides one or more seals that minimizes or eliminates spillage of urine or other fluids therefrom, especially when the container is dropped or tipped.

Further, a need exists for an apparatus for holding urine or other fluids that is easy to use, especially for individuals who may find it difficult to use a bathroom, such as when a bathroom is unavailable or the individual is unable to make it to a bathroom or otherwise use a bathroom.

Still further, a need exists for an apparatus for holding urine or other fluids that is easy to view the contents thereof or readily displays how full it is.

In addition, a need exists for an apparatus for holding urine or other fluids that may contain an absorbent material for further minimizing spillage of the urine or other fluids.

SUMMARY OF THE INVENTION

The present invention relates to a compact portable apparatus for holding urine or other fluids safely and hygienically. Specifically, the present invention provides a container that traps urine or other fluids when deposited therein. The container has one or more seals that allow the container to be sealed after use so that leakage of the container after use may be minimized or eliminated. Moreover, the container has a downwardly sloping passageway for the passage of urine and/or other bodily fluids and an arcuately-shaped or angled backwall for directing a flow or spray of urine or other fluids into a reservoir for holding the same. Moreover, the present invention provides a container having a window for viewing the contents of the container or to determine the quantity of the fluids contained therein. The container may include an absorbent material for absorbing the urine and/or other bodily fluids. The container may be made from a soft, resilient material, such as a flexible thermoplastic material. The present invention further relates to a kit having the container and other components, such as wet napkins, cleaning wipes, sickness bags and/or other like articles. In addition, the present invention relates to methods of using the same.

To this end, in an embodiment of the present invention, an apparatus for holding urine or other fluids is provided. The apparatus comprises an opening on a first end of the apparatus; a backwall within the apparatus disposed on an opposite end of the apparatus; a passageway disposed between the opening and the backwall; an opening in a bottom of the passageway located adjacent the back wall; and a reservoir disposed beneath the passageway, wherein the opening in the bottom of the passageway permits access between the passageway and the reservoir.

In an embodiment, the apparatus comprises a flange forming the bottom of the passageway, wherein the flange further forms a ceiling of the reservoir.

In an embodiment, the apparatus comprises a window in the apparatus for viewing the contents of the reservoir.

In an embodiment, the back wall is arcuately-shaped to direct the flow of fluids into the reservoir from the passageway.

In an embodiment, the apparatus further comprises a handle, wherein the handle is disposed at a balanced location on the container when the container is filled.

In an embodiment, the apparatus further comprises a first seal in the opening, wherein the first seal prevents escape of fluids from the container.

In an embodiment, the apparatus of further comprises a second seal in the passageway, wherein the second seal helps prevent escape of the fluids from the container.

In an alternate embodiment of the present invention, a method of using an apparatus for holding urine or other fluids is provided. The method comprises the steps of providing a container having an opening on a first end of the apparatus, a backwall within the container disposed on an opposite end of the container, a passageway disposed between the opening and the backwall, an opening in a bottom of the passageway located adjacent the back wall, and a reservoir disposed beneath the passageway, wherein the opening in the bottom of the passageway permits access between the passageway and the reservoir; opening the container to provide access to the interior of the container; allowing a flow of fluids to enter the container; and sealing the container to help prevent the escape of the fluids from the container.

In an embodiment, the method further comprises the step of directing the flow of the fluids from the passageway to the reservoir through the opening in the bottom of the passageway.

In an embodiment, the container has a window disposed therein and further the method comprises the step of viewing the contents of the container after filling the container with fluids through the window.

In an embodiment, the back wall of the container is arcuately-shaped and further the method comprises the step of directing the fluids from the passageway along the back wall and through the opening in the bottom of the passageway.

In an embodiment, the container has a handle wherein the handle is disposed at a balanced location on the container when the container is filled with the fluids and further the method comprises the step of holding the container by the handle when filling the container with fluids.

In an embodiment, the container comprises a first seal in the opening, wherein the first seal prevents escape of fluids from the container, further the method comprises the steps of opening the seal prior to filling the container with fluids; and closing the seal after using the container to prevent an escape of the fluids from the container.

In an embodiment, the container comprises a second seal in the passageway, wherein the second seal helps prevent escape of the fluids from the container, further the method comprises the steps of opening the second seal prior to filling the container with the fluids; and closing the second seal after using the container to prevent the escape of the fluids from the container.

In a still further alternate embodiment of the present invention, a kit is provided. The kit comprises an apparatus for holding urine or other fluids comprising an opening on a first end of the apparatus, a backwall within the apparatus disposed on an opposite end of the apparatus, a passageway disposed between the opening and the backwall, an opening in a bottom of the passageway located adjacent the back wall, and a reservoir disposed beneath the passageway, wherein the opening in the bottom of the passageway permits access between the passageway and the reservoir; and a first article.

In an embodiment, the first article is a packet of cleaning wipes.

In an embodiment, the first article is soap.

In an embodiment, the first article is antibacterial fluid.

In an embodiment, the kit further comprises a second article wherein the second article is a motion sickness bag.

In an embodiment, the article is a packet of cleaning wipes and further the kit comprises a motion sickness bag.

It is, therefore, an advantage of the present invention to provide an apparatus for holding urine or other fluids that may be utilized to catch and hold urine, especially from a user in a sitting position.

In addition, it is an advantage of the present invention to provide an apparatus for holding urine or other fluids that may catch and hold a spray of urine or other fluids and may direct the spray of urine or other fluids into a holding area or reservoir.

Moreover, it is an advantage of the present invention to provide an apparatus for holding urine or other fluids that provides one or more seals that minimizes or eliminates spillage of urine or other fluids therefrom, especially when the container is dropped or tipped.

Further, it is an advantage of the present invention to provide an apparatus for holding urine or other fluids that is easy to use, especially for individuals who may find it difficult to use a bathroom, such as when a bathroom is unavailable or the individual is unable to make it to a bathroom or otherwise use a bathroom.

Still further, it is an advantage of the present invention to provide an apparatus for holding urine or other fluids that is easy to view the contents thereof or readily displays the quantity of fluids contained therein.

In addition, it is an advantage of the present invention to provide an apparatus for holding urine or other fluids that may contain an absorbent material for further minimizing spillage of the urine or other fluids.

Additional features and advantages of the present invention are described in, and will be apparent from, the detailed description of the presently preferred embodiments and from the drawings.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE PRESENTLY PREFERRED EMBODIMENTS

The present invention relates to a compact portable apparatus for holding urine or other fluids safely and hygienically. Specifically, the present invention provides a container that traps urine or other fluids when deposited therein. The container has one or more seals that allow the container to be sealed after use so that leakage of the container after use is minimized or eliminated. Moreover, the container has a generally horizontally-disposed downwardly sloping passageway for the passage of urine or other fluids and an angled or arcuately-shaped backwall for directing a flow or spray of urine or other fluids into a holding area or reservoir for holding the same. Moreover, the present invention provides a container having a window for viewing the contents of the container to determine the quantity of fluid contained within the container. Alternatively, the container may include an absorbent material for absorbing the urine or other fluids. The container may be made from a soft, resilient material, such as a flexible thermoplastic material. The present invention further relates to a kit having the container and other components, such as wet napkins, cleaning wipes, sickness bags and/or other like articles. In addition, the present invention relates to methods of using the same.

Figure 1:
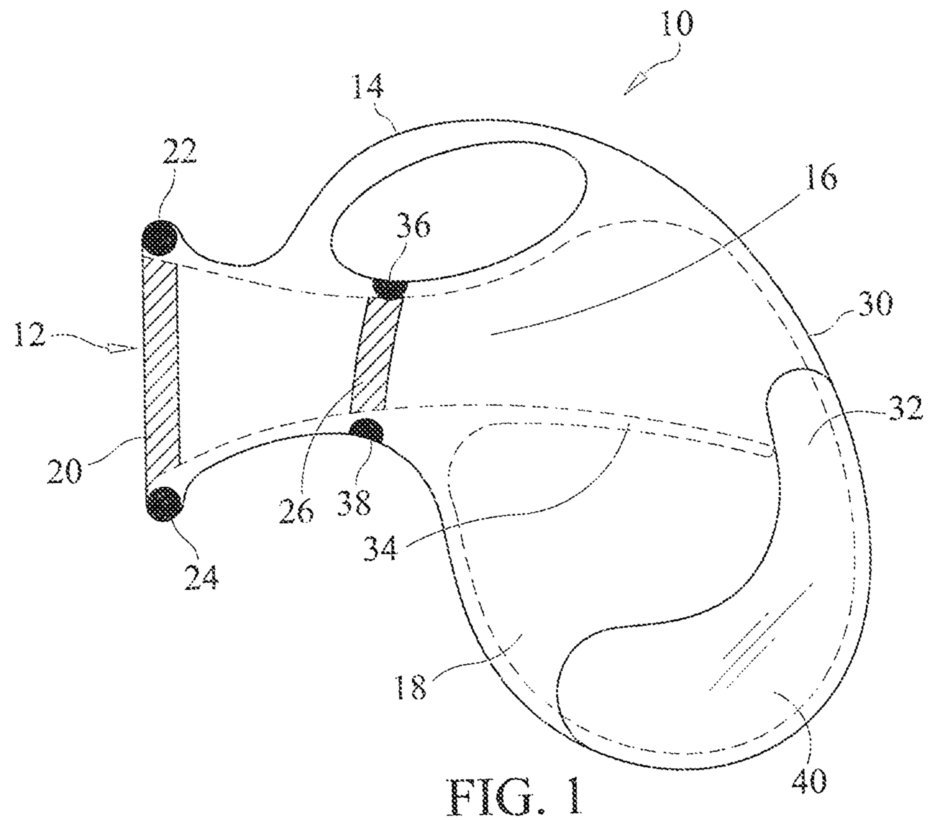
FIG. 1 illustrates a side view of an apparatus container for holding urine or other fluids in an embodiment of the present invention.
Figure 2:
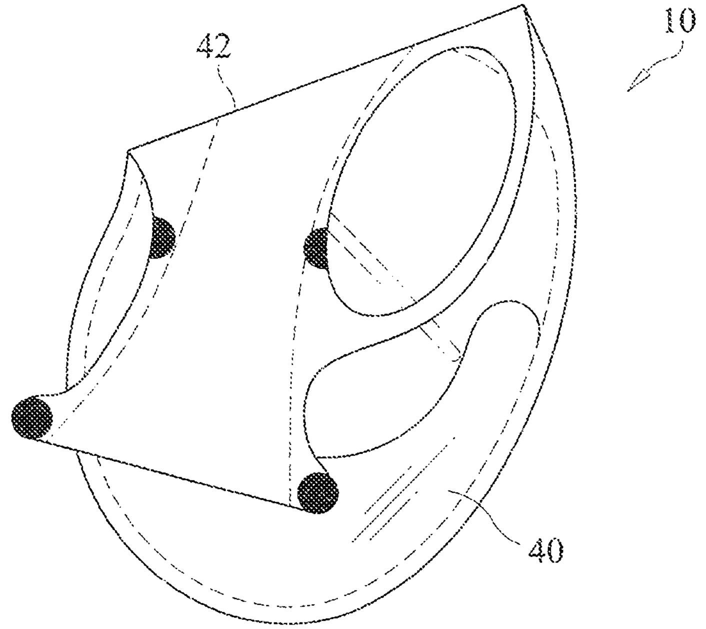
FIG. 2 illustrates a perspective view of an apparatus for holding urine or other fluids that is folded in an embodiment of the present invention.

FIG. 1 illustrates a side view of a container 10 in an embodiment of the present invention. The container 10 may preferably be made of a soft thermoplastic material that is flexible and easily foldable, as illustrated in FIG. 2. Specifically, the container includes an opening 12 disposed on an end of the container. The opening 12 may be utilized by an individual to urinate thereinto, or otherwise deposit fluids therein, such as bodily fluids. The opening 12 may include a pair of strips 20 of rigid thermoplastic material that may generally be closed. Pushing on buttons 22, 24 allows the strips 20 to open, providing access to the interior of the container 10 for depositing urine or other fluids thereinto. Once used, the strips 20 may be allowed to return to their original state, disposed immediately adjacent each other to effectively seal the opening 12. Of course, other mechanisms for providing an opening 12 are contemplated by the present invention, such as plastic zippers, hook and loop fasteners, adhesives and other like means.

Adjacent the opening 12 may be a passageway 16 running from the opening 12 to a back wall 30 at an end of the container 10 opposite the opening 12. The passageway 16 may direct the urine or other bodily fluids from the opening 12 into a reservoir 18 disposed immediately beneath the passageway 16. Urine or other fluids may flow through the passageway 16 and be deposited into the reservoir 18 through an opening 32 between the passageway 16 and the reservoir 18. The opening 32 provides access to the reservoir 18 for the urine or other fluids. The opening 32 further restricts access of the urine or other bodily fluids from returning to the passageway 16 after being deposited into the reservoir 18. Specifically, a flange 34 may be disposed on a bottom of the passageway 16 extending nearly to the back wall 30 and forming the opening 32 with the back wall 30. The flange 34 further acts as an upper ceiling to the reservoir 18.

Moreover, the back wall 30 may be contoured to direct the flow of urine or other bodily fluids into the reservoir 18. Preferably, the back wall 30 may be angled or arcuately shaped to direct the flow of urine or other bodily fluids. Specifically, the back wall 30 may direct a spray of urine or other fluids, especially if traveling the passageway 16 at an increased velocity as a spray, for example.

The passageway 16 further may include a second pair of strips 26 disposed at an intermediary position in the passage 16. Normally, the pair of strips 26 may be disposed immediately adjacent each other forming a seal. However, pushing buttons 36, 38 may open the pair of strips 26 allowing access through the passageway 16 for the urine or other bodily fluids. After use, the pair of strips 26 may be allowed to return to being immediately adjacent each other, forming a second seal that restricts access of the urine and or other fluids from returning to the opening 12 and escaping from the container 10. Of course, other mechanisms for closing the passageway 16 may be utilized and are contemplated by the present invention, such as plastic zippers, hook and loop fasteners, adhesive and/or other like means for closing the passageway 16 at the intermediary position.

A window 40 may be disposed in the container 10 allowing a user or other individual to view the contents of the container 10. Specifically, the window 40 may be made from a transparent or translucent material indicating the fullness of the container 10. A user may identify the quantity of the fluid in the container 10, and provide an indication whether the container 10 may be used one or more additional times to hold urine or other bodily fluids. For example, if upon use of the container 10, the container 10 is not full, then it may be used a second time or more times by opening the mouth, the pair of strips 20 and pair of strips 26. Alternatively, measurement marks (not shown) may be provided on the window or other location of the container 10 to provide a more accurate measurement of the quantity of the fluid contained therein.

An absorbent material (not shown) may be contained within the container 10 for absorbing the urine or other like fluids contained therein. Specifically, a gel or powder may be utilized that readily absorbs urine or other fluids, thereby restricting the escape of the urine or other bodily fluids from the container 10. Alternatively, an absorbent material may be incorporated into the thermoplastic material of the container 10 for holding urine or other fluids deposited thereinto.

The container 10 may further include a handle 14 disposed generally at a location to aid in the carrying or holding of the container before, during and/or after use. The handle 14 may preferably be disposed at the container's center of gravity, thereby making the holding and/or carrying of the container easier, especially when filled with urine or other fluids. The handle 14 may be made from a thermoplastic material. Preferably, the handle 14 may be reinforced to aid in the holding of the container 10 when filled so that the handle does not tear or otherwise break away from the container when being held by a user.

As shown in FIG. 1, the structure of the container 10 generally allows the passageway 16 to maintain a generally horizontal position when used. Therefore, a user of the container 10 may simply allow a user's member to be horizontally placed thereinto allowing the flow of urine or other fluids thereinto. Because the container 10 may be positioned to provide the passageway 16 with a generally horizontal positioning, the container 10 may be ideally suited for use when an individual is sitting or in an otherwise prone position, such as if the individual is in a seated position in an automobile or truck, for example. The handle 14 further allows the container 10 to be held providing the passageway 16 to be disposed in the generally horizontal position. Moreover, the placement of the reservoir 18 relative to the opening 12 and the passageway 16 may allow the reservoir to hang over an edge of a seat when in use.

FIG. 2 illustrates a perspective view of a container 10 in a folded arrangement, such as prior to use. Specifically, the container 10 may have a fold line 42 disposed therein, such as a line of weakness, or other like folding means, for easily folding the container 10 when not in use. Folding the container 10, especially after use, provides an additional mechanism for sealing the urine or other fluids therein and restricting escape of the urine or other fluids contained therein.

Figure 3:
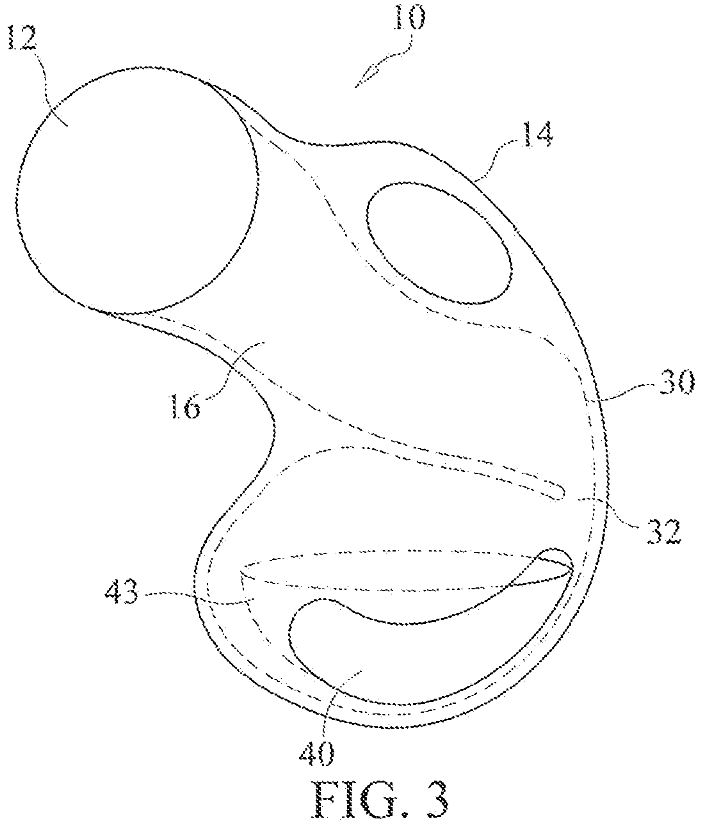
FIG. 3 illustrates a perspective view of an apparatus for holding urine or other fluids having a quantity of fluid therein in an embodiment of the present invention.

FIG. 3 illustrates a perspective view of the container 10 illustrating the opening 12. The opening 12 and the passageway 16 creates a funnel shape that is preferably wide enough to prevent direct contact of a user's member and/or allowing all shapes and sizes of members to be disposed therein. As illustrated, the handle 14 may be positioned to allow a user to hold the container 10 in a balanced position, when in use and/or when filled. Further, the back wall 30 may be contoured to direct the flow of urine or other fluids into the reservoir 18 and prevent sprayback of the urine or other bodily fluids. The opening 32 between the back wall 30 and the flange 34 acts to prevent spills in case of accidentally dropping or tipping the container 10, especially before the container 10 is sealed or otherwise disposed. Further, the container 10 includes the window 40 that allows the user to check the contents of the container 10 and preserving the discreet shape of the container. A quantity of fluid 43 is shown contained therein.

Figure 4:
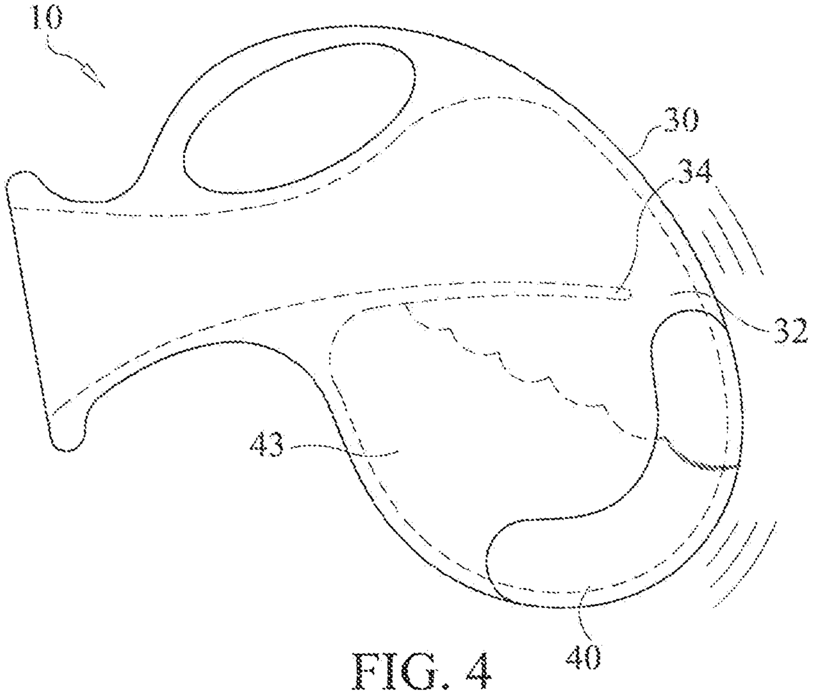
FIG. 4 illustrates a perspective view of an apparatus for holding urine or other fluids in a tipped position in an embodiment of the present invention.

FIG. 4 illustrates the container 10 having been tipped. As illustrated, the flange 34, the opening 32 and the back wall 30 operate in concert to prevent spillback of the urine or other bodily fluid contained therein when tipped or accidentally dropped, especially prior to sealing the container 10.

Figure 5A:
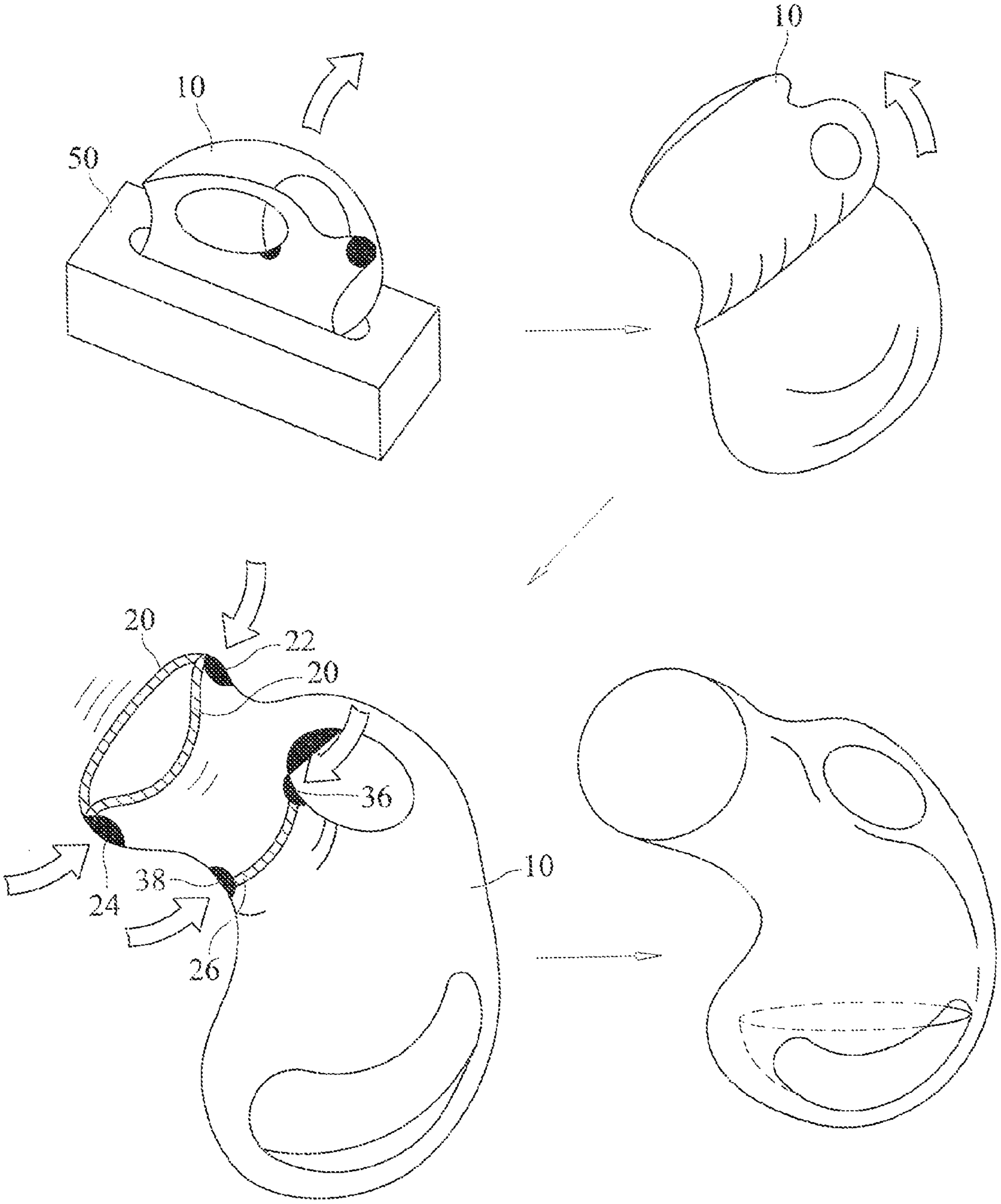
FIG. 5 illustrates an apparatus for holding urine or other fluids and a method of using the same in an embodiment of the present invention.
Figure 5B:
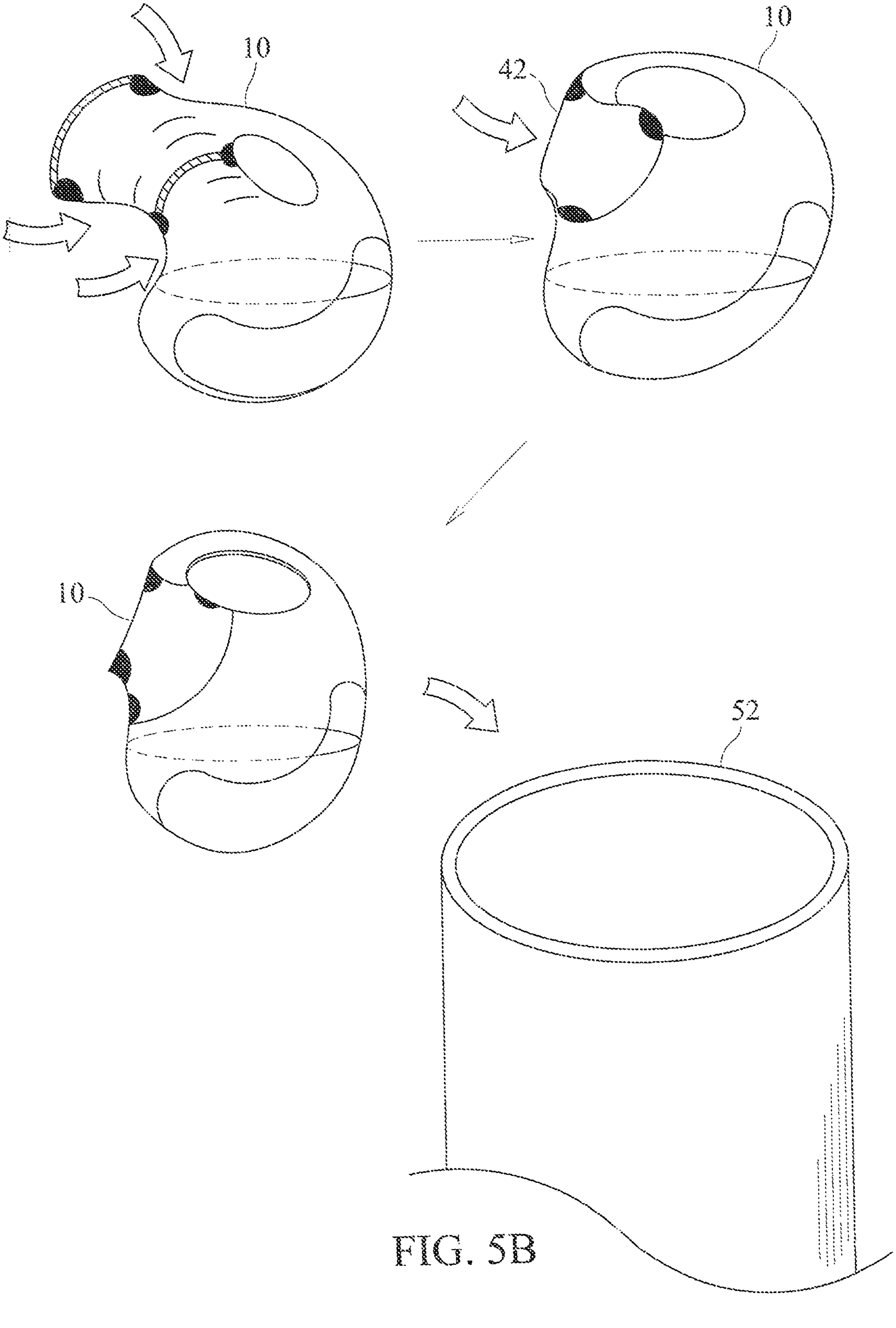

FIGS. 5A and 5B illustrate a preferred method of using the container 10. Specifically, the container 10 may be contained within a box 50 or other holder. A plurality of containers of the present invention may be provided within the box 50. A user may pull the container 10 from the box 50 and the container 10 may be in a folded configuration. The container 10 may be unfolded prior to use. The buttons 22, 24 and 36, 38 may be pressed thereby opening the pairs of strips 20 and 26 to obtain access to the passageway 16 and, hence, the reservoir 18. As illustrated, the container 10 may be ready for use and filled with urine or other fluids.

FIG. 5B illustrates a method for closing and disposing of the container 10. After use, the container 10 may be closed and sealed by allowing the pairs of strips 20 and 26 to come together and seal the urine or other fluid contained therein. The pairs of strips 20, 26 may preferably be closeable with a single hand. Therefore, an individual may hold the container 10 by the handle 14 with one hand, and the container may be sealed by closing the pairs of strips 20, 26 with the other hand. The container 10 may then be folded along fold line 42 thereby providing an additional seal to prevent escape of the urine or other fluids contained therein. The container may then be deposited in a garbage can 52 or other refuse container for disposal thereof.

Figure 6:
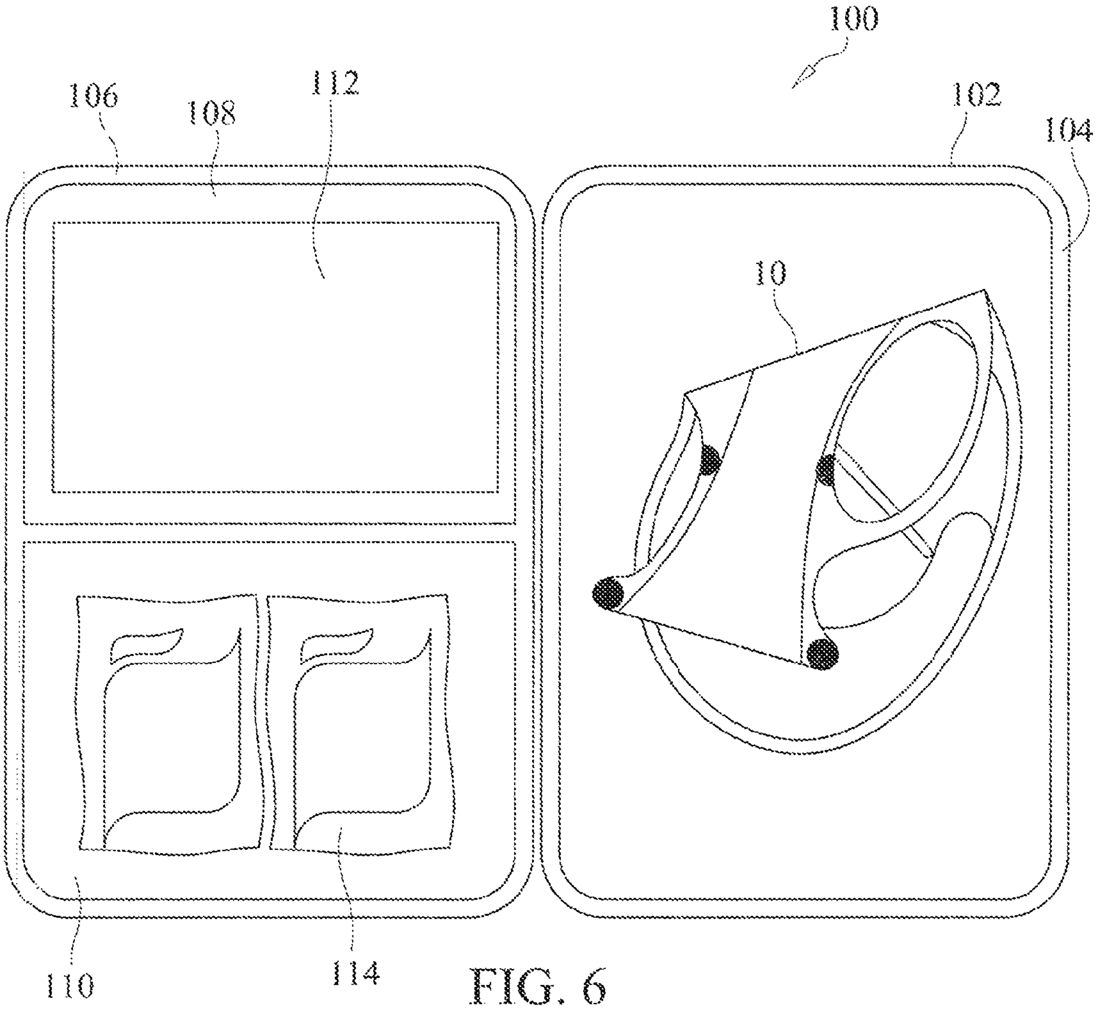
FIG. 6 illustrates a kit having an apparatus container for holding urine or other fluids and other articles in an embodiment of the present invention.

FIG. 6 illustrates a kit 100 in an embodiment of the present invention. The kit 100 may include a box 102 or other like holder. The box 102 may have a first side 104 and a second side 106 for holding articles, as described herein. The first side 104 may include one or more containers 10 for holding urine or other fluids as described herein, preferably in a folded state for ease of storage. The second side 106 of the box 102 may further have a first receptacle 108 and a second receptacle 110 for storage of other articles useful for a user of the container 10. Of course, a plurality of receptacles, such as more than two, may be contained within the first side and/or the second side, as may be apparent to one having ordinary skill in the art, for holding articles therein.

For example, as illustrated in FIG. 6, receptacle 108 may contain a sickness bag 112 for use in, for example, an automobile, boat, plane or other like vehicle when the individual has motion sickness. Moreover, the receptacle 110 may contain one or more packets of cleaning wipes, tissues, soap, antibacterial fluid or other like articles 114 useful for cleaning a user, such as after use. The kit 100 allows sanitary and hygienic use of the container 10, the sickness bag 112 and/or other like articles. Preferably, the box 102 is hinged and openable when necessary for use. It should be noted that other articles may be contained within the box 102 and may be part of the kit 100 as apparent to one having ordinary skill in the art.

It should be noted that various changes and modifications to the presently preferred embodiments described herein will be apparent to those skilled in the art. Such changes and modifications may be made without departing from the spirit and scope of the present invention and without diminishing its attendant advantages.

I claim:

1. An apparatus for holding urine or other fluids comprising:
- an opening on a first end of the apparatus;
- a back wall within the apparatus disposed on an opposite end of the apparatus;
- a passageway horizontally disposed between the opening and the back wall
- an opening in a bottom of the passageway located adjacent the back wall;
- a handle for holding the apparatus when filling the container, wherein the handle is disposed at a balanced location on the container for holding the container when the container is filling with fluids; and
- a reservoir disposed beneath the passageway, wherein the opening in the bottom of the passageway permits access between the passageway and the reservoir;
- wherein the apparatus is made from a flexible material and further wherein the apparatus has a flattened configuration and an expanded configuration for receiving the urine or the other fluids.

2. The apparatus of claim 1 further comprising:
- a flange forming the bottom of the passageway, wherein the flange further forms a ceiling of the reservoir.

3. The apparatus of claim 1 further comprising:
- a window in the apparatus for viewing the contents of the reservoir.

4. The apparatus of claim 1 wherein the back wall is arcuately-shaped to direct the flow of fluids into the reservoir from the passageway.

5. The apparatus of claim 1 further comprising:
- a first seal in the opening, wherein the first seal prevents escape of fluids from the container.

6. The apparatus of claim 5 further comprising:
- a second seal in the passageway, wherein the second seal helps prevent escape of the fluids from the container.

7. A method of using an apparatus for holding urine or other fluids comprising the steps of:
- providing a malleable container having a flattened configuration and an expanded configuration wherein, when is said expanded configuration, further having an opening on a first end of the apparatus, a back wall within the container disposed on an opposite end of the container, a passageway horizontally disposed between the opening and the back wall, an opening in a bottom of the passageway located adjacent the back wall, a handle wherein the handle is disposed at a balanced location on the container when the container is filling with the fluids, and a reservoir disposed beneath the passageway, wherein the opening in the bottom of the passageway permits access between the passageway and the reservoir;

opening the container to provide access to the interior of the container, wherein opening the container changes the flattened configuration into the expanded configuration;

allowing a flow of fluids to enter the container;

holding the container by the handle when filling the container with fluids; and sealing the container to help prevent the escape of the fluids from the container.

8. The method of claim 7 further comprising the step of:

directing the flow of the fluids from the passageway to the reservoir through the opening in the bottom of the passageway.

9. The method of claim 7 further wherein the container has a window disposed therein and further comprising the step of:

viewing the contents of the container after filling the container with fluids through the window.

10. The method of claim 7 wherein the back wall is arcuately-shaped and further comprising the step of:

directing the fluids from the passageway along the back wall and through the opening in the bottom of the passageway.

11. The method of claim 7 further wherein the container comprises a first seal in the opening, wherein the first seal prevents escape of fluids from the container, further comprising the steps of:

opening the seal prior to filling the container with fluids; and closing the seat after using the container to prevent an escape of the fluids from the container.

12. The method of claim 11 further wherein the container comprises a second seal in the passageway, wherein the second seal helps prevent escape of the fluids from the container, further comprising the steps of:

opening the second seal prior to filling the container with the fluids; and closing the second seal after using the container to prevent the escape of the fluids from the container.

* * * * *